US012788637B2

(12) United States Patent
Lipshaw et al.

(10) Patent No.: US 12,788,637 B2
(45) Date of Patent: *Nov. 10, 2026

(54) GRADUATED COMPRESSION DEVICE FOR THE TREATMENT OF CIRCULATORY DISORDERS

(71) Applicant: MEDI MANUFACTURING, INC., Whitsett, NC (US)

(72) Inventors: Moses Lipshaw, Hillsborough, NC (US); Thomas Richardson, San Diego, CA (US); Teresa Kennerknecht, San Diego, CA (US); Sandra Anne Shaw, Coronado, CA (US)

(73) Assignee: Medi Manufacturing, Inc., Whitsett, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/569,975

(22) Filed: Mar. 17, 2026

(65) Prior Publication Data

US 2026/0207391 A1 Jul. 23, 2026

Related U.S. Application Data

(60) Continuation of application No. 19/332,806, filed on Sep. 18, 2025, now Pat. No. 12,629,289, which is a continuation of application No. 18/489,748, filed on Oct. 18, 2023, now Pat. No. 12,564,520, which is a division of application No. 17/969,279, filed on Oct. 19, 2022, now Pat. No. 11,826,238, which is a
(Continued)

(51) Int. Cl.
*A61F 13/08* (2006.01)

(52) U.S. Cl.
CPC .................................. *A61F 13/085* (2013.01)

(58) Field of Classification Search
CPC .......... A61F 13/00059; A61F 13/00051; A61F 13/108; A61F 13/00034; A61F 13/00038; A61F 13/00021; A61F 13/00025; A61F 13/00029; A61F 13/0269; A61F 13/0273; A61F 13/00004; A61F 13/84; A61F 13/62; A61F 13/08; A61F 2013/00148; A61F 2013/00131; A61F 2013/00565; A61F 2013/00276; A61F 2013/00102; A61F 2013/00093; A61F 2013/00119; A61F 2013/00123; A61F 2013/00153; A61F 2013/00089; A61F 2013/8497; A61F 15/00
See application file for complete search history.

(56) References Cited

U.S. PATENT DOCUMENTS 4,297,997 A * 11/1981 Clayton ............ A61M 25/1002 602/61
4,697,285 A * 10/1987 Sylvester .................. F41H 1/02 2/2.5
(Continued)

*Primary Examiner* — Camtu T Nguyen
(74) *Attorney, Agent, or Firm* — Rimon PC

(57) ABSTRACT

A therapeutic compression garment, including: a body portion; and a spine portion, wherein the bands extending from either the body portion and/or spine portion attach the body and spine portions together when the body and spine portions are wrapped around a body limb, and wherein the spine portion is releasably attached onto the body portion such that the spine portion is positionable at different locations on the body portion.

8 Claims, 17 Drawing Sheets

Related U.S. Application Data division of application No. 17/207,584, filed on Mar. 19, 2021, now Pat. No. 11,529,263, which is a continuation of application No. 16/131,936, filed on Sep. 14, 2018, now Pat. No. 10,980,675, which is a continuation of application No. 12/952,065, filed on Nov. 22, 2010, now Pat. No. 10,117,784.

(60) Provisional application No. 61/264,213, filed on Nov. 24, 2009.

(56) References Cited

U.S. PATENT DOCUMENTS

| | | | | | |
|---|---|---|---|---|---|
| 4,753,228 | A | * | 6/1988 | Selner | A61F 13/066<br>36/89 |
| 4,836,194 | A | * | 6/1989 | Sebastian | A61F 5/028<br>128/DIG. 20 |
| 5,734,992 | A | | 4/1998 | Ross | |
| 5,755,679 | A | * | 5/1998 | Selner | A61F 5/0111<br>602/65 |
| 10,980,675 | B2 | * | 4/2021 | Lipshaw | A61F 13/085 |
| 11,529,263 | B2 | * | 12/2022 | Lipshaw | A61F 13/085 |

* cited by examiner

GRADUATED COMPRESSION DEVICE FOR THE TREATMENT OF CIRCULATORY DISORDERS

RELATED APPLICATIONS

The present invention is a continuation of U.S. application Ser. No. 19/332,806, filed on Sep. 18, 2025, which is a continuation of U.S. application Ser. No. 18/489,748, filed on Oct. 18, 2023, which is now U.S. Pat. No. 12,564,520, which is a divisional of U.S. application Ser. No. 17/969,279, filed Oct. 19, 2022, which is now U.S. Pat. No. 11,826,238, which is a divisional of U.S. application Ser. No. 17/207,584, filed Mar. 19, 2021, which is now U.S. Pat. No. 11,529,263, which is a continuation of U.S. application Ser. No. 16/131,936, filed Sep. 14, 2018, which is now U.S. Pat. No. 10,980,675, which is a continuation of U.S. patent application Ser. No. 12/952,065, filed Nov. 22, 2010, which is now U.S. Pat. No. 10,117,784, which in turn claims priority to U.S. Provisional Patent Application No. 61/264,213, entitled "Graduated Compression For The Treatment Of Circulatory Disorders", filed Nov. 24, 2009, the entire disclosures of which are incorporated by reference herein in their entirety.

TECHNICAL FIELD

The present invention relates to devices that treat circulatory disorders such as lymphedema, edema and venous diseases.

BACKGROUND OF THE INVENTION

A common treatment for circulatory disorders such as lymphedema, edema and venous diseases is to wear a compression garment. Current compression garments are available in various ready-to-wear standard sizes. Unfortunately, a wide array of inventory must be kept on hand when distributing ready-to-wear garments in order to accommodate the population majority. Although compression garments have been designed that can be modified in circumference or length to obtain a better fit, the "nearest" size must still be chosen.

Alternatively, custom made-to-measure garments have also been produced as a form of treatment. Unfortunately, measuring, sizing, and ordering these made-to-measure garments is time consuming and may still not result in a properly fitted compression garment. For limbs that are outside of the standard ready-to-wear size range, custom garments need to be built to match the curvature, length and circumference of the limb. As a result, many measurements are needed to make these custom garments and there is a period between measuring, ordering, production and fitting of the garment where the limb profile may change, which can result in an improper fit due to the time it takes for the patient to receive their garment.

Various compression garments have tried trimming-to-fit methods where longer bands are cut down from the largest size to fit the patient. Unfortunately, these bands need to be trimmed separately or in pairs and angled in a manner that best conforms to the shape of the limb. This is a slow and time consuming process. Working out the correct lengths and angles of each band can be very difficult, and is often made more difficult due to the fact that the bands need to overlap to obtain complete coverage.

Other compression modalities such as bandaging have also been used. An advantage of bandaging is that it can be used on 100% of the population with one inventory set. Unfortunately, bandaging is very time consuming and does not have the benefit of quick and easy application as compared to standard compression garments. In addition, bandaging is not guaranteed to provide reliable/consistent compression levels, and cannot be adjusted as the limb shape and compression needs change.

SUMMARY OF THE INVENTION

The present invention provides a one-size-fits-all compression garment that can easily and quickly be tailored to match the circumference profile of a particular patient's limb.

In a preferred embodiment, the present invention provides a therapeutic compression garment, comprising: a body portion having a plurality of bands extending from one side; and a spine portion having a plurality of bands extending from one side, wherein the bands extending from the body portion and the bands extending from the spine portion attach the body and spine portions together when the body and spine portions are wrapped around a body limb, and wherein the spine portion is releasably attached onto the body portion such that the spine portion is positionable at different locations on the body portion. The present invention provides therapeutic compression. The spine portion is attached to the body portion at a preferred location, such that the garment best fits the particular patient's limb.

The therapeutic compression garment may be fit onto a patient's limb by first measuring the circumference of the patient's limb at a top location, at a bottom location, and then the length of the limb. Next, the garment is assembled around the limb by: (i) aligning the spine portion and the body portion using measurement indicia (on one or the other of the body or spine portions); (ii) attaching the spine portion onto the body portion; (iii) optionally discarding an unused portion of the body portion; and then (iv) wrapping the assembled therapeutic compression garment around the patient's limb, thereby securing the bands in their proper location.

It is to be understood throughout the specification that the present invention may be used on either a patient's arm or leg, and that examples referring to a leg are merely exemplary, and not limiting.

Preferably, hook and loop fasteners are used such that the body and spine portions are first attached together by hook and loop fasteners. After this has been done, the two piece device will then become a continuous one piece garment. Next, the resulting one piece garment will then be positioned behind the limb and the open front side will then be wrapped and fastened together around the front of the patient's limb. Preferably, the hook and loop fasteners holding the body and spine portions together are stronger than the hook and loop fasteners holding the bands to the body and spine portions when the garment is applied. Thus, pulling on the bands to tighten, adjust, or remove the garment will not cause the body and spine portions to pull apart. Therefore, the user will be less likely to unintentionally disengage to the spine attachments while detaching the other bands.

In preferred embodiments, the top and bottom edges of the body portion are marked with measurement indicia and a curved edge of the spine portion is aligned with these measurement indicia, as follows. First, the top of the spine portion is aligned with the measurement indicia on the body portion corresponding to the circumference measurement taken at the top location on the patient's limb, and the bottom of the spine portion is aligned with the measurement indicia on the body portion corresponding to the circumference measurement taken at the bottom location on the patient's limb. The spine portion is then attached onto the body portion by one or more hook and loop fastener tabs (positioned along a curved edge of the spine portion). In other embodiments, the measurement indicia are displayed along the mid portions of either the spine or body portions. In the various embodiments of the present invention, these measurement indicia correspond to the circumference of a particular patient's body limb, or to general body limb sizes such as small, medium, large and extra large.

In various embodiments, after the body and spine portions have been fastened together (but prior to wrapping the garment around the patient's limb), if necessary the user simply discards the unused portion by cutting off the excess.

An advantage of the present garment is that it can be provided in one size for all patients (since the actual sizing and adjustment of the garment can be done by the therapist or end user or clinician). Another advantage of the present garment is that it is simple to put on and very easy for a clinician or end user to shape, size correctly, and adjust accordingly.

DETAILED DESCRIPTION OF THE DRAWINGS

Figure 1A:
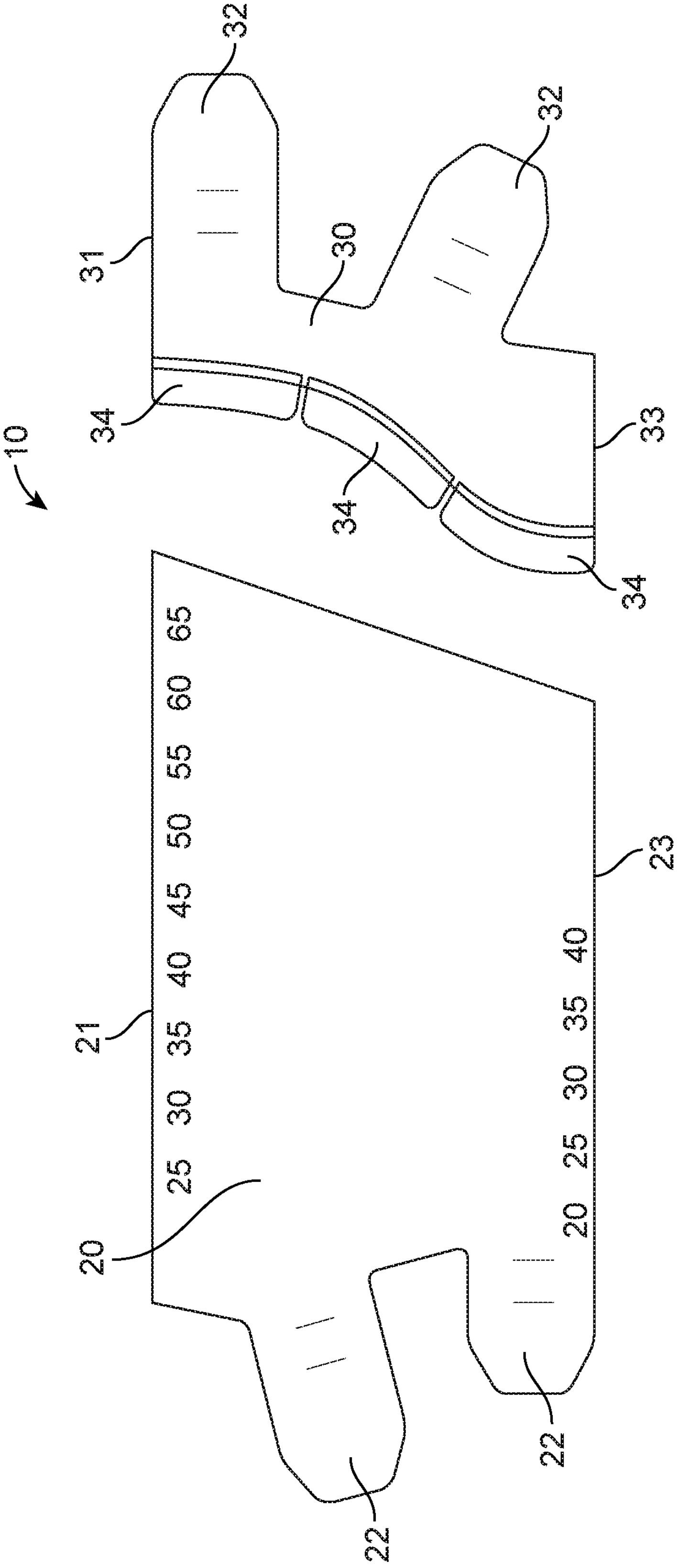
FIG. 1A is an illustration of the garment prior to attaching the body and spine portions together.
Figure 1B:
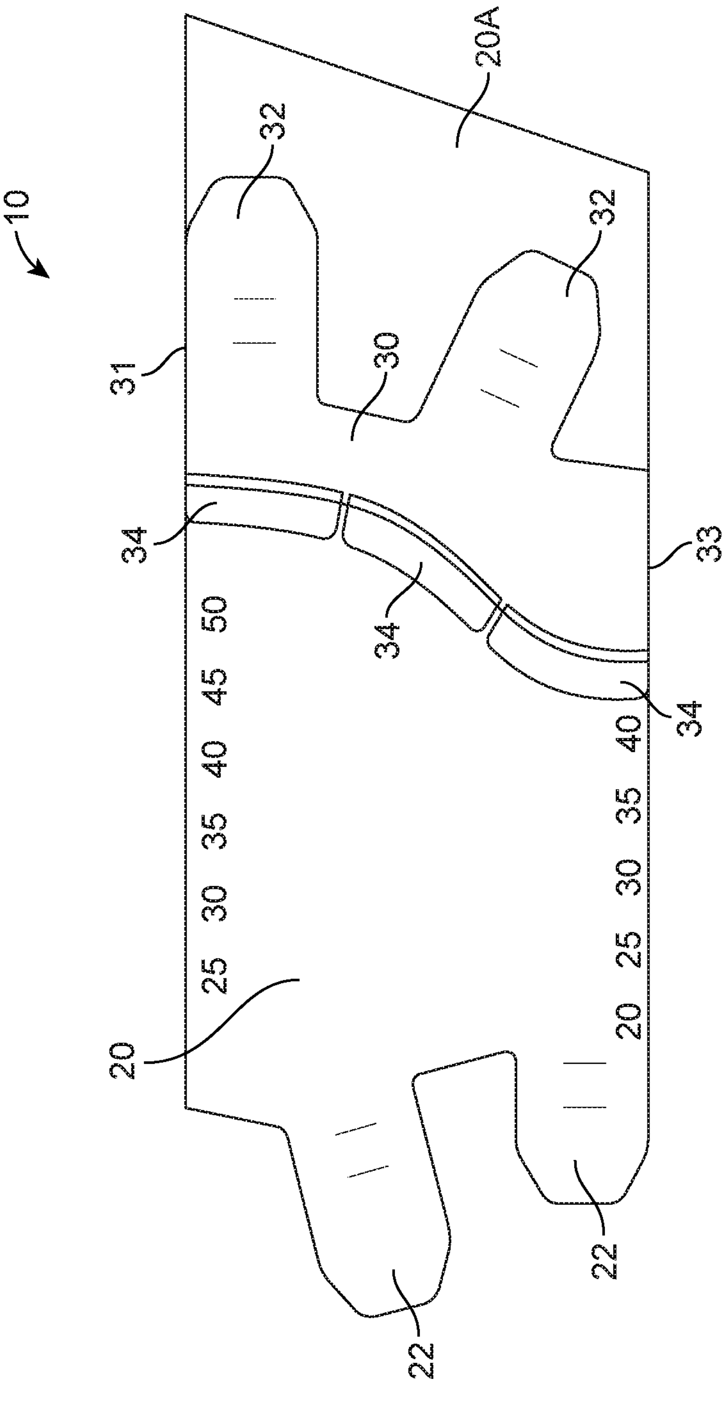
FIG. 1B is an illustration of the garment after attaching the body and spine portions together.
Figure 2A:
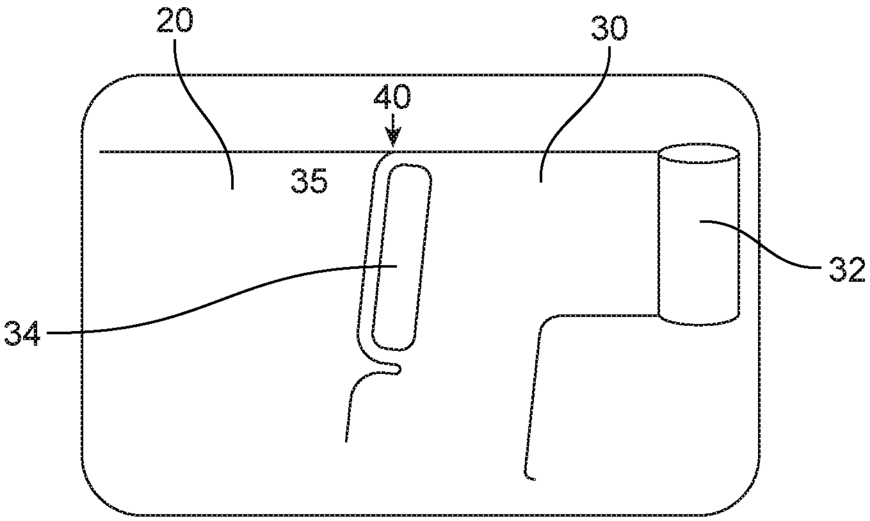
FIG. 2A is a close up of the top of the garment showing the alignment of the body and spine portions.
Figure 2B:
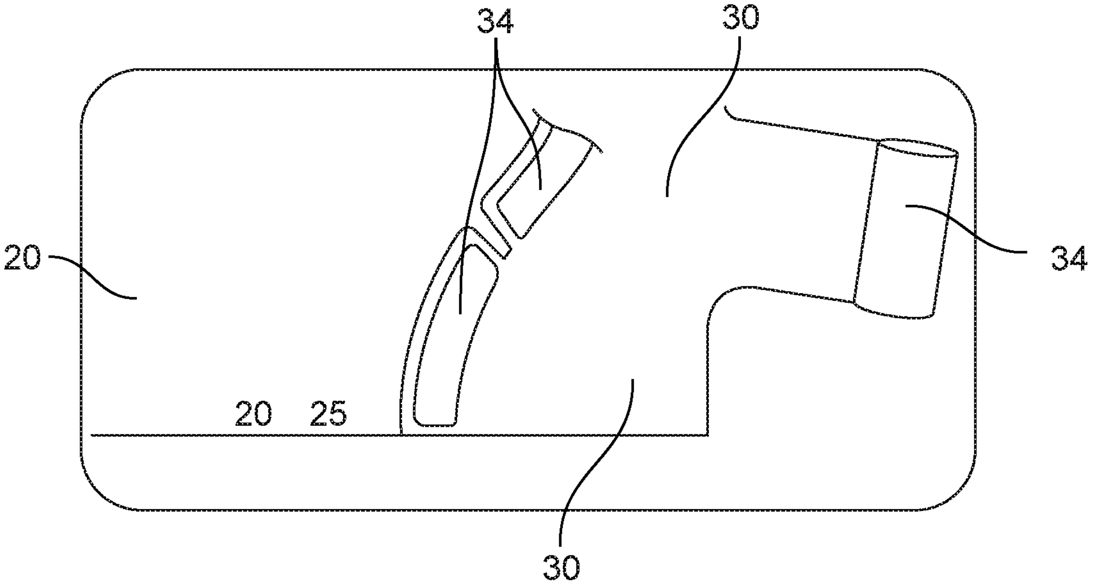
FIG. 2B is a close up of the bottom of the garment showing the alignment of the body and spine portions.

Referring first to FIGS. 1A to 5B, a therapeutic compression garment 10 is provided. Garment 10 comes in two pieces, being a body portion 20 and a spine portion 30. Body portion 20 has a plurality of bands 22 extending from one side as shown. Spine portion 30 similarly has a plurality of bands 32 extending, from one of its sides as shown.

Figure 5B:
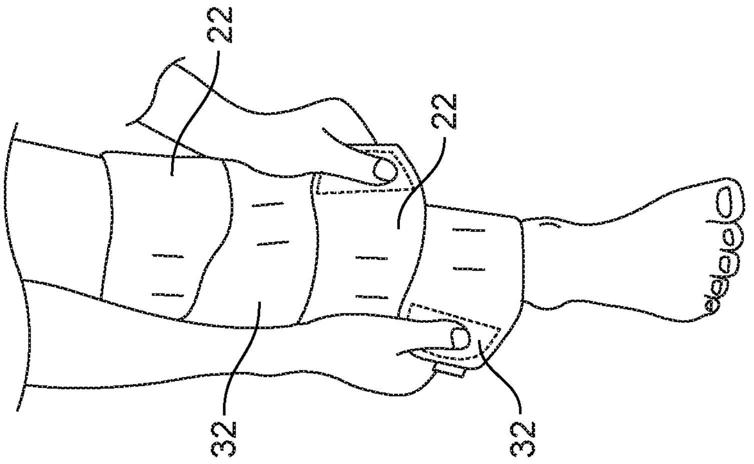
FIGS. 5A and 5B are sequential illustrations of the patient wrapping the garment around their leg.
Figure 5A:
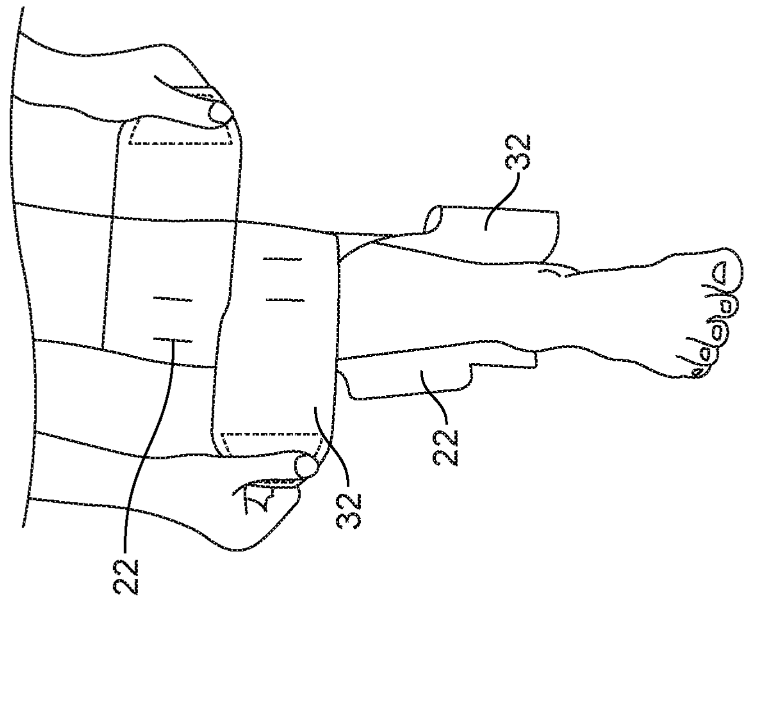

As will be explained, the bands 22 extending from body portion 20 are juxtaposed between the bands 32 extending from spine portion 30 when garment 10 is wrapped around the patient's limb. Specifically, as seen in FIGS. 5A and 5B, bands 22 are fastened onto spine portion 30 and bands 32 are fastened onto body portion 20. Most preferably, bands 22 and 32 have Velcro® (i.e.: hook and loop fastener) ends. Similarly, the surfaces of body portion 20 and spine portion 30 are also covered with corresponding Velcro® (i.e.: hook and loop fastener) surfaces. In some embodiments, bands 22 and 32 may extend past the spine divider (i.e.: the connection point between the body and spine portions) and back onto their own portions respectively.

In operation, the therapeutic compression garment 10 is fitted onto a patient's limb, as follows. First, the patient (or other person assisting the patient) measures the circumference of the limb at a top location and at a bottom location and the length of the limb. For example, the limb would be the leg, the top location would be the calf, the bottom location would be the ankle, and the leg length from ankle to knee crease would determine the preferred garment length.

Figure 4:
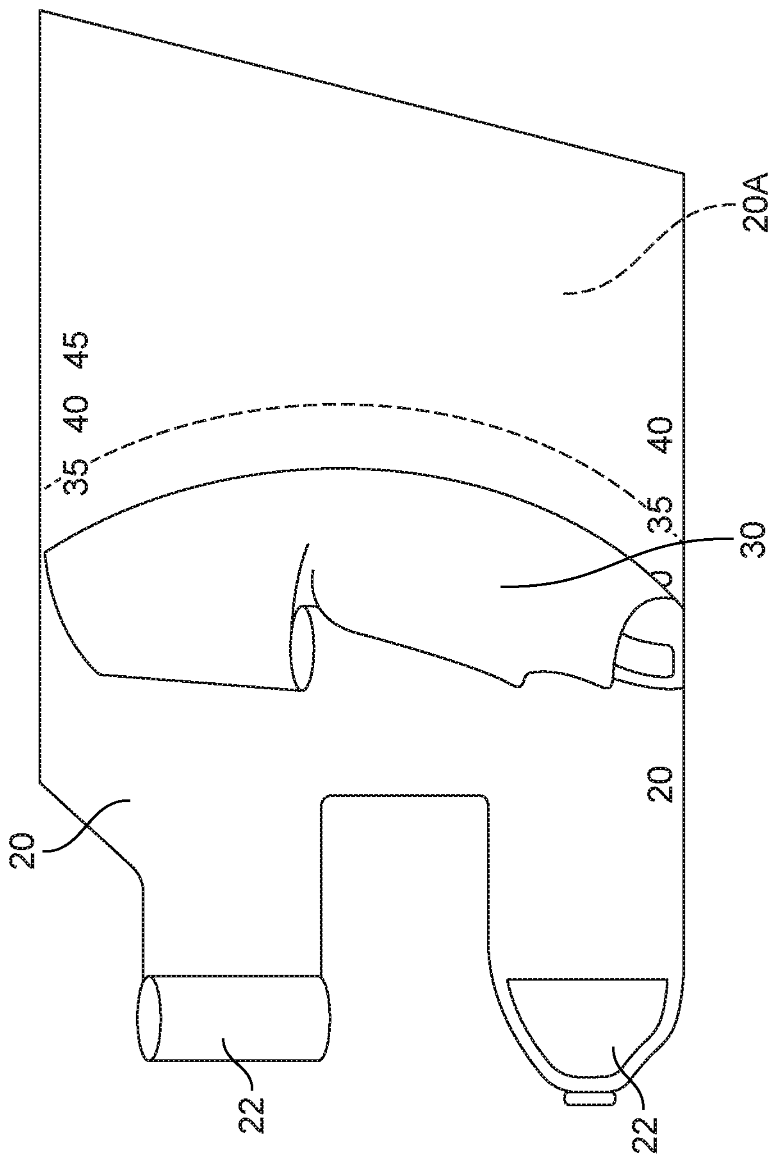
FIG. 4 is an illustration of discarding an unused portion of the body portion after the body and spine portions have been attached together.

Next, the patient assembles therapeutic compression garment 10 around their limb by: (i) aligning spine portion 30 with the measurement indicia on body portion 20 (as seen in close up FIGS. 2A and 2B); (ii) attaching spine portion 30 onto body portion 20; (iii) discarding any unused portion of body portion 20; and then (iv) wrapping the assembled therapeutic compression garment 10 around their leg (while juxtaposing bands 22 and 32 thereby securing bands 22 onto spine portion 30 and bands 32 onto body portion 20). As a result, the two piece garment shown in FIG. 1A is first changed into the one-piece garment shown in FIG. 1B. Next, as shown in FIG. 4, an unused portion 20A of body portion 20 is discarded. Finally, as shown in FIGS. 5A and 5B, garment 10 is wrapped around the patient's leg.

Figure 3C:
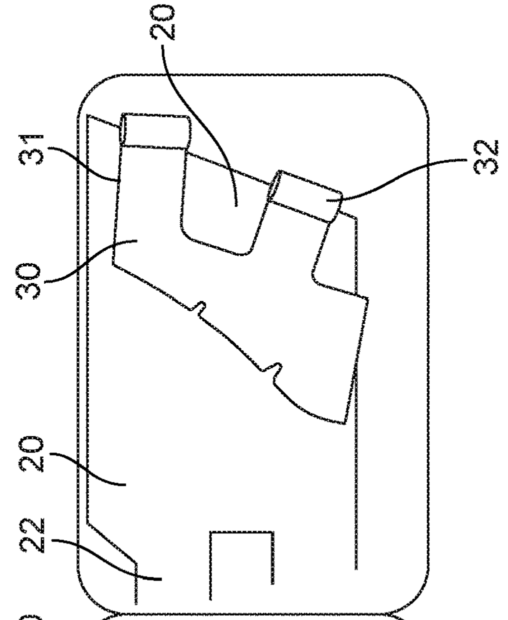
FIG. 3C is an illustration of a third alignment of the body and spine portions (as suited for a patient having a small ankle and large calf).
Figure 3B:
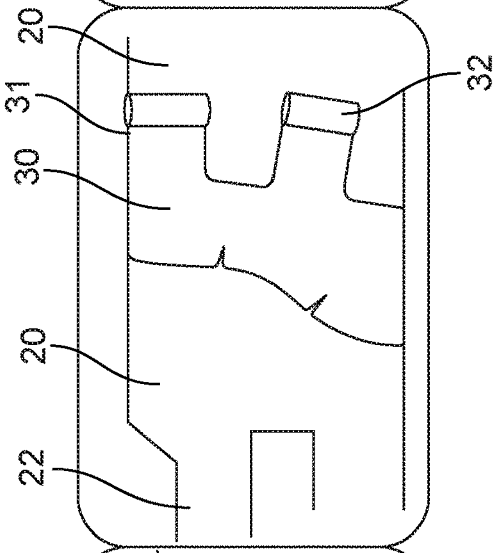
FIG. 3B is an illustration of a second alignment of the body and spine portions (as suited for a patient having a small ankle and medium calf).
Figure 3A:
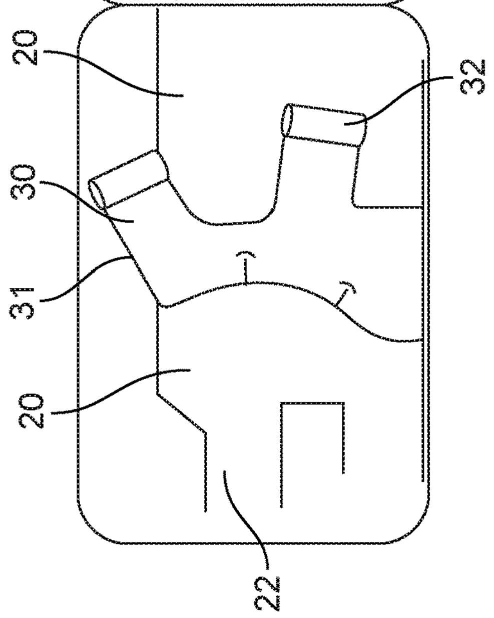
FIG. 3A is an illustration of a first alignment of the body and spine portions (as suited for a patient having a small ankle and calf).

As can be seen in FIGS. 3A to 3C, spine portion 30 is releasably attached onto body portion 20. As a result, spine portion 30 is positionable at different locations on body portion 20. This permits spine portion 30 to be positioned at different locations depending upon the dimensions of the patient's limb. Preferably, body and spine portions 20 and 30 are simply attached together by hook and loop fasteners. As illustrated, spine 30 may have three fastener tabs 34 disposed along the curved edge of spine 30 (opposite to the side from which bands 32 extend). The spacing selected between fastener tabs 34 allows the spine curve (i.e.: the connection along which the body and spine portions 20 and 30 are attached together by fastener tabs 34) to be positioned such that garment 10 starts to take a three dimensional shape (as opposed to simply lying flat). This shaping helps the garment to best fit the contours of the limb.

As can be seen, body portion 20 preferably has parallel top edge 21 and bottom edge 23. These top and bottom edges 21 and 23 of the body portion are marked with measurement indicia. As seen in the close up view of FIGS. 2A and 2B, the curved edge of spine portion 30 is aligned with the measurement indicia on the top and bottom edges 21 and 23 of body portion 20. Aligning spine portion 30 with the measurement indicia on body portion 20 comprises aligning the top 31 of spine portion 30 with the measurement indicia on the top 21 of body portion 20 corresponding to the circumference measurement taken at the top location on the patient's limb (e.g.: at the calf). Similarly, aligning spine portion 30 also comprises aligning the bottom 33 of spine portion 30 with the measurement indicia on the bottom 23 of body portion 20 corresponding to the circumference measurement taken at the bottom location on the patient's limb (e.g.: at the ankle).

Fitting is done by measuring the patient's ankle and calf circumferences. These circumference measurements are represented by a range of indicia markings along the top edge 21 and bottom edge 23 of body portion 20. The bottom markings reflect the ankle circumference and the top markings reflect the calf circumference. The hook tabs 34 from spine portion 30 are secured to body portion 20 according to where the patient's ankle and calf circumference measurements fall within the marked ranges. Each tab 34 can be angled independently due to spacing between the tabs and any elasticity in the material used. This allows spine tabs 34 to be further adjusted to create smooth transitions from top to bottom along spine portion 30. The spine's already curved edge aids in mimicking the limb's natural contour. This feature, along with adjustable spine tabs 34, allows the garment to adjust to almost any limb size and shape.

As seen in FIGS. 3A to 3C, a variety of different alignment positions are possible (since each position will depend upon the exact ankle and calf measurements of the particular patient). Specifically, FIG. 3A illustrates a patient having a small ankle and calf. FIG. 3B illustrates a patient having a small ankle and medium calf. FIG. 3C illustrates a patient having a small ankle and large calf, though any variation of leg proportions can be addressed. After spine portion 30 has been properly aligned, it is then simply pressed against body portion 20 such that it is held in position by hook and loop fasteners 34. (Note: the side of body portion 20 and spine portion 30 is preferably covered with a hook and loop fastener surface.)

Next, as shown in FIG. 4, spine portion 30 is simply pulled back aside, and the patient/clinician then cuts off the unused portion (designated 20A) of body portion 20. Thus, the unused portion 20A is removed from a side opposite to the side from which bands 22 extend.

Next, as seen in FIGS. 5A and 5B, the assembled garment 10 is then wrapped around the front of the leg, thereby securing bands 22 onto spine portion 30, and securing bands 32 onto body portion 20. Thus, bands 22 are simply fastened onto spine portion 30 by hook and loop fasteners. Similarly, bands 32 are attached to body portion 20 by hook and loop fasteners. Preferably, the hook and loop fasteners holding the body and spine portions 20 and 30 together are stronger than the hook and loop fasteners holding the bands 22 and 32 to either of the body and spine portions 20 or 30. As a result, tightening, adjusting, or disengaging bands 22 and 32 at the front of the garment does not pull apart the body and spine portions 20 and 30 at the back of the garment. The preferred difference in hook and loop strength provides the user with additional guidance as to which hook tabs should be disengaged while doffing or adjusting the therapeutic garment. Optionally, one or more reinforcement tabs 40 (see FIG. 11A) can also be used to further secure the body and spine portions 20 and 30 together. Reinforcement tabs 40 can similarly be made of hook and loop fastener surfaces such that they can attach directly on top of body and spine portions 20 and 30 (to reduce the risk of the spine-to-body connection being disengaged along the back of the garment).

The hook and loop fasteners may be secured directly on to the surface of (i.e.: sewn onto) the ends of bands 22 and 32. In contrast, the hook and loop fasteners may optionally extend from the edges of the body and spine portions 20 and 30. As a result, the addition of the hook and loop fasteners onto the body and spine portions 20 and 30 would not add any significant thickness to the final garment, reducing the risk of accidental spine tab 34 removal.

As illustrated, there are three tabs 34. It is to be understood that the invention encompasses any number of tabs 34. For example, using additional smaller tabs (e.g.: four or more) can better match the limb profile, however more adjustments would be necessary. The adhesion strength of the spine to body portion connection may also be reduced due to the increased number of spine tabs 34. Conversely, using fewer tabs 34 (one or two) decreases the ability for the spine to contour to the limb because current hook material available is inelastic in nature and doesn't bend easily. If an elastic pliable hook were to be used, the entire curved portion of spine portion 30 could be made from one tab.

Alternatively, garment 10 may be provided to the user with portions 20 and 30 already fastened together (via bands 22 and 32 fastened to opposing body portion 20 and spine portion 30). In this situation, fitting would be done by holding the free end of the body portion 20 against the limb and wrapping the garment around the limb so that spine portion 30 encircles the limb and overlaps back onto the outside of the free end of body portion 20. Spine portion 30 is then attached to body portion 20 so that the garment is as snug as possible. Further fitting is achieved by pulling on each individual hook tabs 34 in order to mimic the limb contour and further shape the fit of the garment to match the shape of the limb.

Once the garment has been fitted and the body and spine portions are fully secured together, the garment is removed by disengaging the juxtaposed bands 22 and 32. Once removed, the body-to-spine attachment can further be secured by smoothing out the material or making minor adjustments for clean transitions between the spine hook tabs 34. The excess material can be trimmed following the inside edge of the spine hook tabs 34.

Figure 6A:
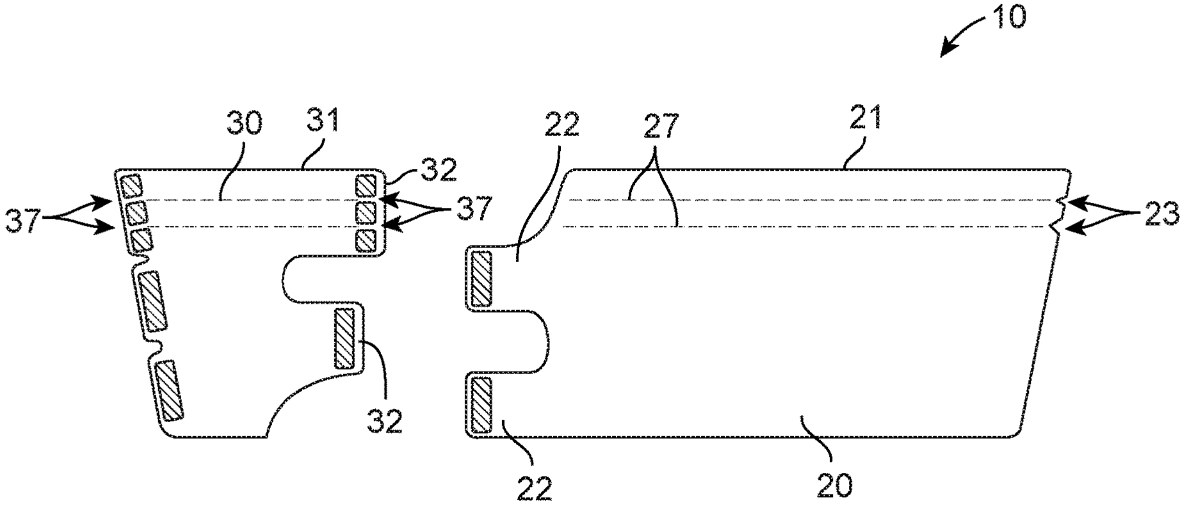
FIGS. 6A and 6B are a second embodiment of the present invention.
Figure 6B:
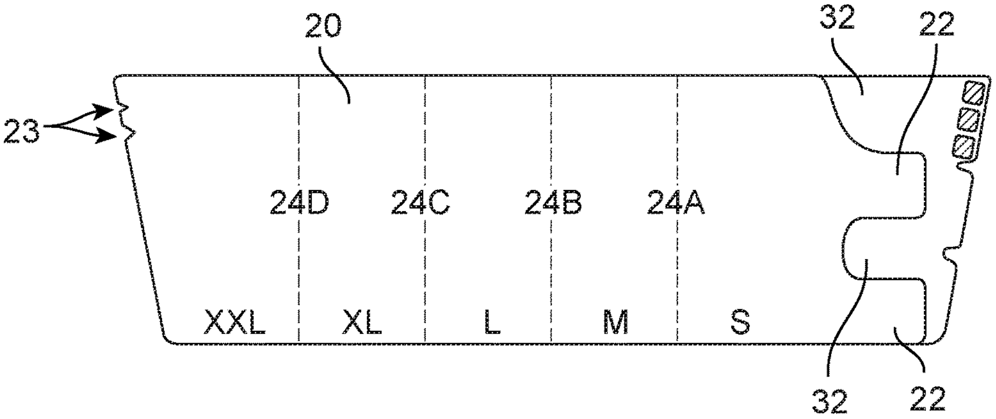

FIGS. 6A and 6B illustrate a second embodiment of the invention in which spine portion 30 has a straight edge opposite to the side from which bands 32 extend. Specifically, FIG. 6A shows an interior (i.e.: surface to be put against the skin) of the garment. FIG. 6B shows a corresponding exterior view after bands 22 and 32 have been attached onto the outside surface of the garment. In previous Figures, a curved edge on spine 30 increases the ability of the spine portion 30 to contour to the limb. This is because the circumference at the ankle is generally smaller than the circumference at the calf, which creates a curved contour. Thus, the curved edge spines (seen in FIGS. 1A to 5B) best match the curves of the limb profile. In contrast, the use of a straight spine (FIGS. 6A and 6B) would force the material to stretch and adjust more than with a curved spine. Thus, in the embodiment of FIGS. 6A and 6B, garment 10 is preferably made out of elastic or limited stretch material. As also seen in FIGS. 6A and 6B, body portion 20 may have cut away tabs 23 permitting a user to cut away a top (or bottom) portion of the device, thereby shortening the length of the device on the body limb. Specifically, the user could cut off a portion of the height of the device by cutting horizontally across body portion 20 along dotted line one of dotted lines 27. Similarly, cut away tabs may be found on spine portion 30 to trim the height of spine portion 30. Alternatively, as illustrated, the Velcro® fasteners on the ends of band 32 may have gaps 37 there between. Should the user wish to trip the height of the garment (i.e.: it's length along the body limb), the user could cut off a portion of the height of the device by cutting horizontally across spine portion 30 along one of the illustrated dotted lines.

Also in this embodiment, body portion 20 has measurement indicia that designate more general sizes such as small, medium, large and extra-large (S, M, L, XL). Lines can be drawn from top to bottom on body 20 such that a user with a "small" leg cuts along a line 24A whereas a user with a "medium" leg cuts along a line 24B to discard portion 20A. Such lines 24A, 24B, etc. provide a "rough guide" as to the size of portion 20A to discard. Note: similar lines (which may either be markings or perforations) could be used with the garment of FIG. 1A as a method of removing a significant portion of the unused body portion 20A prior to performing a final adjustment to the spine location thus allowing the patient to easily test the spine placement before removing the remaining portion of the body portion 20.

One advantage of the present system is that the need for time-consuming length adjustments is eliminated. Instead, only two predetermined length models (i.e.: body portion 20 and spine portion 30) need to be stocked. This advantageously decreases needed inventory space.

Currently all adjustable designs in the market rely on trimming band length and/or adjusting its angle to fit the garment to the limb. The current invention adjusts the body of the garment to match the contour of the limb independently of any band adjustment. Current compression garments with spines or a second set of bands that are used for adjustment have overlapping adjustment points which make them difficult to use. In contrast, the present invention requires the securing of only three tabs 34 and the trimming of one piece 20, as compared to the trimming and angling of several bands.

In existing compression devices, length adjustment is typically done by cutting off a complete set of bands. In contrast, the present invention trims the width of a band so as to keep gradient compression and not to cut through any assembled materials that could fail due to the cut. In addition, the present invention is a one-layer system, as compared to the three or four layers typically used in bandaging approaches.

Regardless of compression band engagement design (overlap, juxtaposition, interlock, d-ring, etc.), the present design can be converted to a one-size-fits-all garment. It will also match the leg contour regardless of where the fit is made circumferentially on the limb. If the user applies the fitting spine to the shin area while fitting, but then positions it to the back of the calf so the compression bands are easily accessible in the shin area for application, the garment will still match the contour of the limb.

All previous compression garment models rely on a spine or curve point that is centrally/symmetrically located on the garment. For trim to fit versions, material is cut equally on each side of the garment or from band ends. In contrast, the present invention is unique in that it can quickly and easily be adjusted to match the contour of the limb with or without falling on a central point in the garment.

Fitting and applying the garment to appropriate compression can typically be done in less than five minutes. This is far superior to the time involved with bandaging a limb, sizing and fitting a standard size garment, or measuring and producing a custom-made garment.

Optionally, the present invention also includes a "Built-In Pressure System™" and guide card. The patient's ankle circumference measurement determines the appropriate range on the Built-In Pressure System card for the patient. This eliminates the need to translate the patient's ankle circumference into a nominal size, furthermore simplifying the fitting process. The Built-in Pressure System card allows the patient to adjust the garment to the prescribed amount of compression.

Figure 7A:
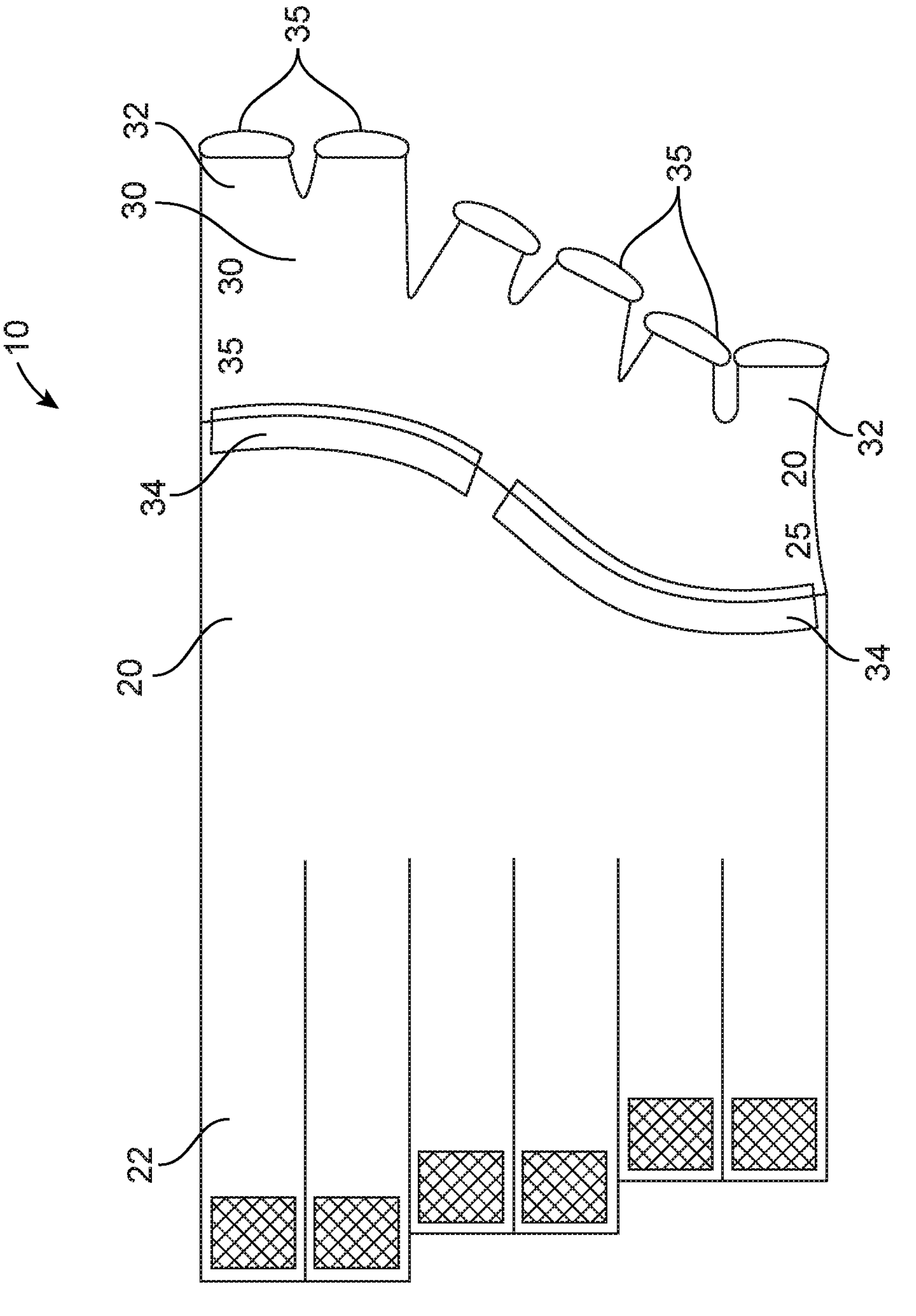
FIGS. 7A and 7B are third embodiments of the present invention.

FIG. 7A is a third embodiment of the present invention in which garment 10 has D-rings 35 attached to the ends of bands 32. In this embodiment, the ends of bands 22 are placed through D-rings 35 and then attached back onto themselves. As can be seen in this embodiment, the bands 32 can be quite short, and may simply be short projections on spine portion 30 onto which the D-rings 35 are attached. As can also be seen, bands 22 can be quite long in this embodiment as they are long loops of materials that weave through D-rings 35 and then attached back upon themselves. The advantage of such a D-ring system is that it allows the patient to tighten the garment using only one hand. Note as well that the measurement indicia are found on spine portion 30 in this embodiment of the invention. Only two spine tabs 34 are used.

Figure 7B:
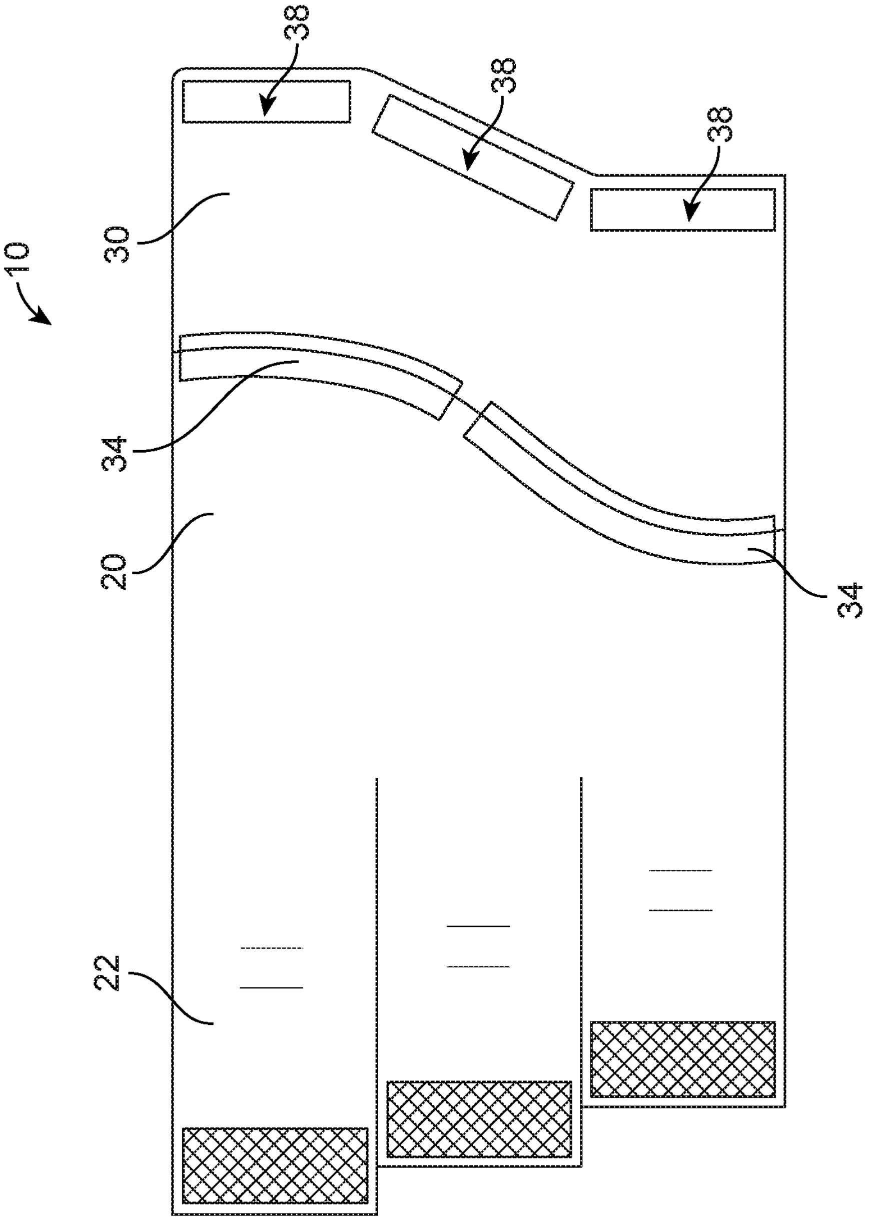

FIG. 7B is quite similar to FIG. 7A, however, instead of D-rings on the ends of bands, the spine portion 30 instead has holes 38 passing therethrough. Bands 22 are passed through holes 38, and are then looped back upon themselves. FIG. 7B illustrates the fact that the present invention is not limited to devices that have bands extending from both of the body and spine portions. Instead, either of the body and spine portions need not have bands extending therefrom, all keeping within the scope of the present invention.

Figure 8:
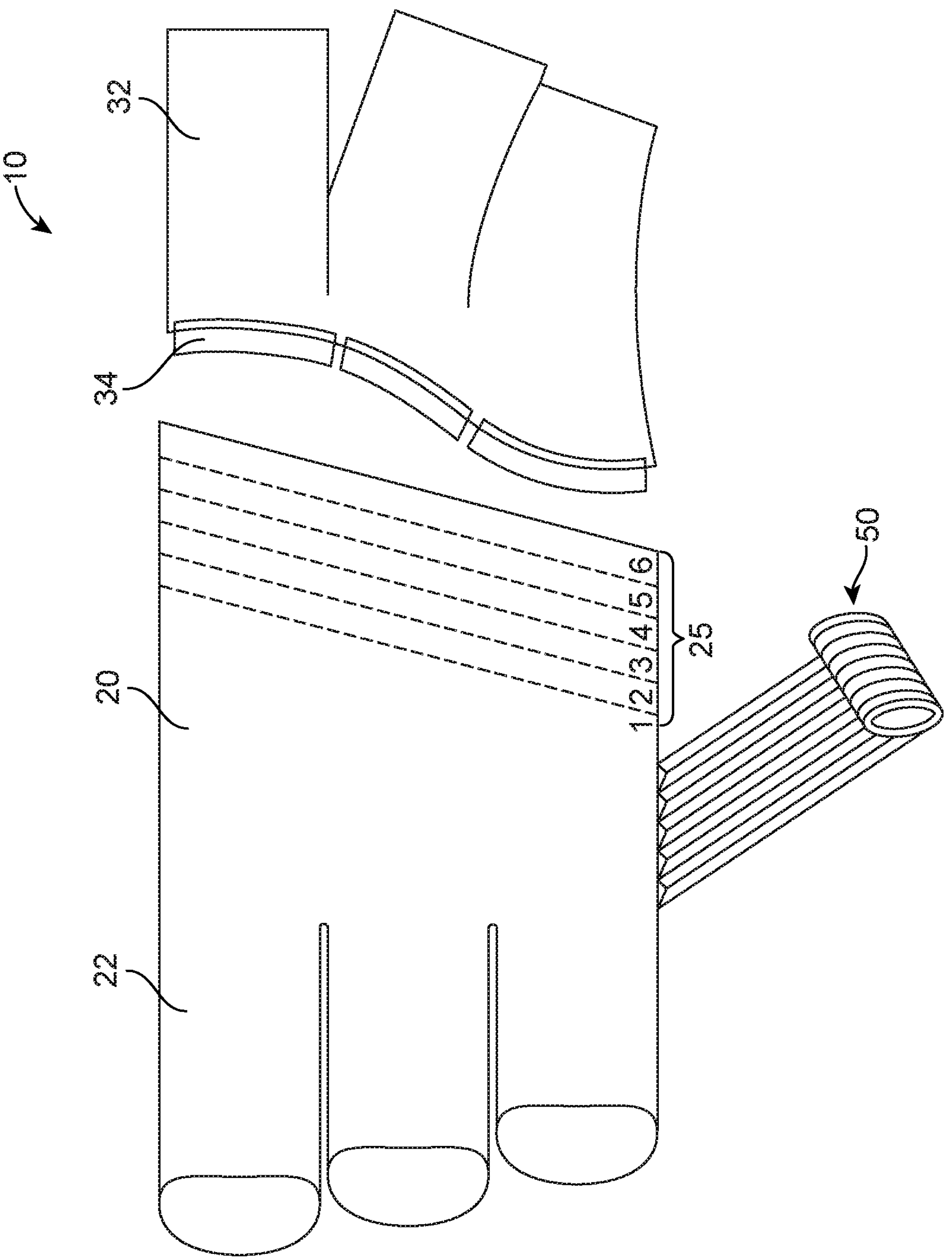
FIG. 8 is a fourth embodiment of the present invention.

FIG. 8 is a fourth embodiment of the present invention in which garment 10 has bands 22 and 32 which are not juxtaposed between one another. Instead, each band 22 is simply fastened onto a respective band 32 (preferably by Velcro® hook and loop fasteners). Body portion 20 has a plurality of numbered perforations (lines 1, 2, 3, 4, 5, 6) allowing unused portion 20A to be removed more easily. This embodiment further includes an elastic wrap 50 for applying compression to an area of the limb that would be difficult to cover (such as the foot or hand), or where flexibility is needed (such as the elbow or knee). Elastic wrap 50 could also be used to cover the junction between garments when using two garments 10 to cover different segments of the limb. It could also be made of a nonslip material to anchor the garment in place and extend from the top of the garment instead.

Figure 9:
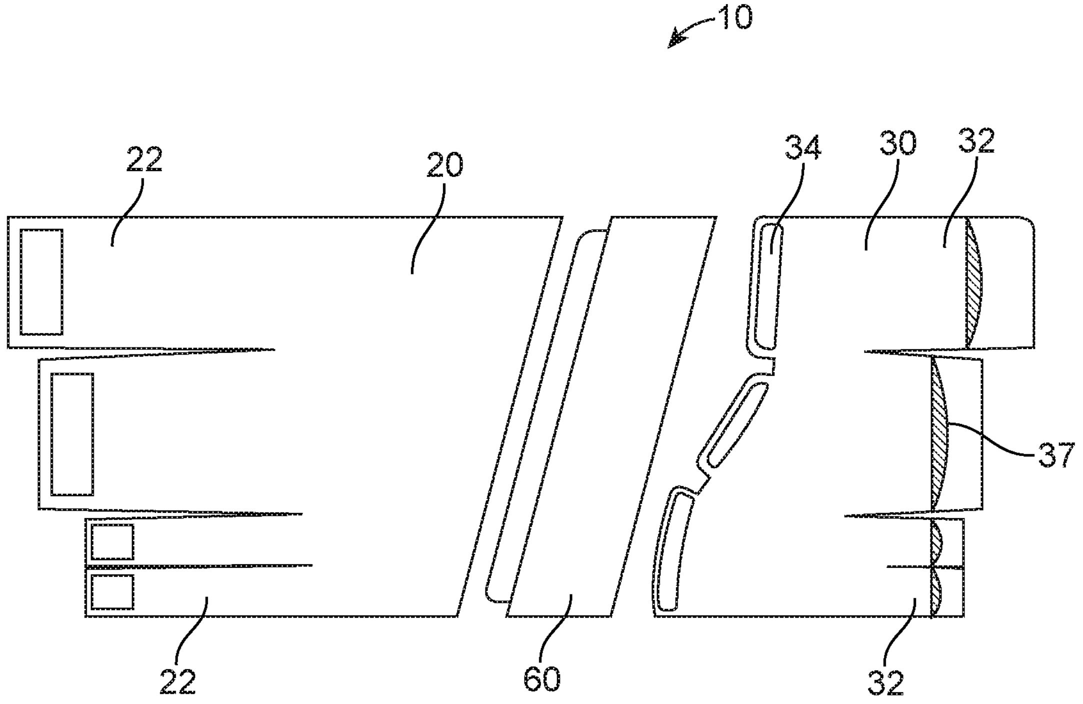
FIG. 9 is a fifth embodiment of the present invention.

FIG. 9 is a fifth embodiment of the present invention in which garment 10 has an intermediary portion 60 is positioned between body portion 20 and spine portion 30. Preferably, intermediary portion 60 is attached to body portion 20 by hook and loop fasteners, and spine portion 30 is attached to intermediary portion 60 by hook and loop fasteners. Thus, body and spine portions 20 and 30 are connected together by way of intermediary portion 60. A number of intermediary portions 60 can be kept on hand to prevent the waste of cut away portions 20A as the patient's limb changes in circumference over time. As can also be seen, bands 22 and 32 may be made of different widths along the length of the garment (for example with narrower bands at the ankle/wrist and wider bands at the calf/elbow), as shown. Also in this embodiment, bands 32 may have pockets 37 that can be used to hold one side of the garment in place while the other side is wrapped over and attached.

Figure 10:
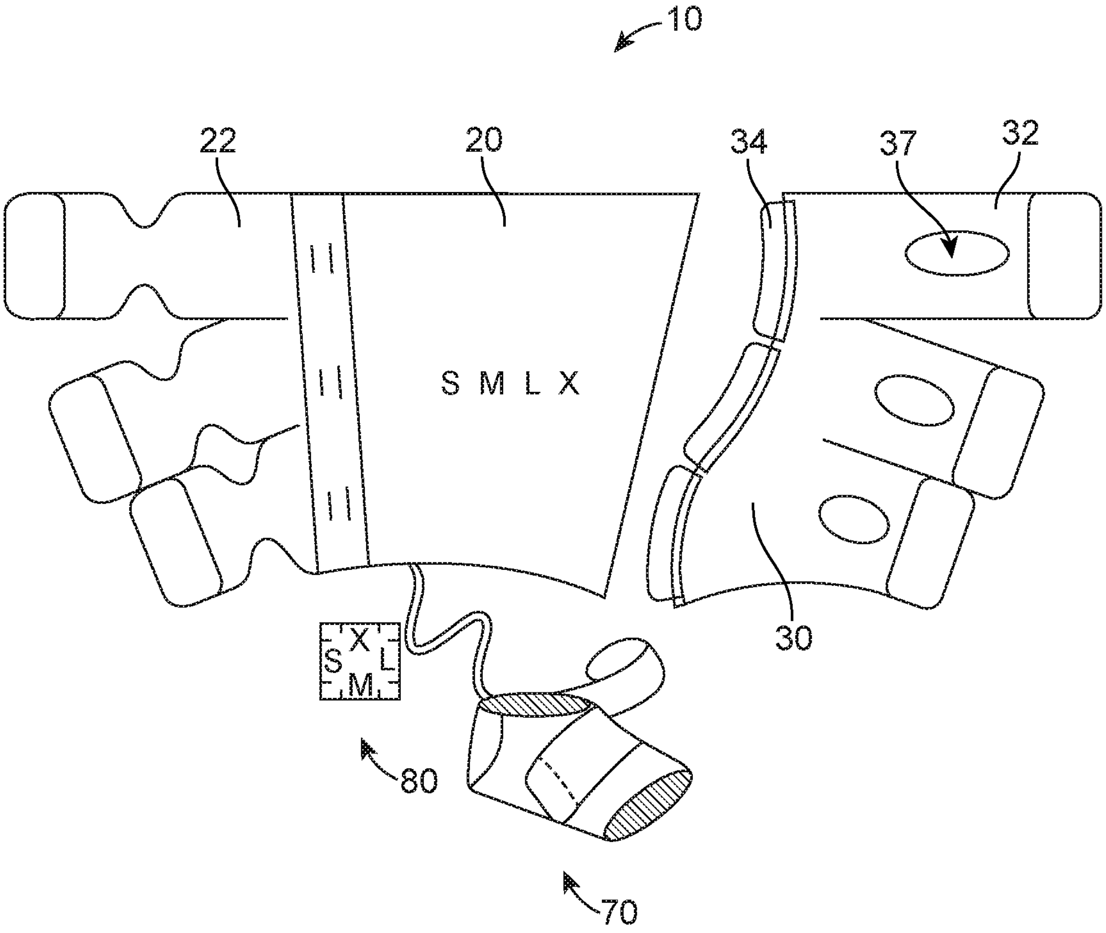
FIG. 10 is a sixth embodiment of the present invention.

FIG. 10 is a sixth embodiment of the present invention in which garment 10 has bands 22 having ends that are received through holes 37 in bands 32. Such interlocking bands provide conformity to the shape of the body limb. Also included is an ankle/foot wrap portion 70 for applying compression to the ankle-foot region. As can also be seen, there are indicia (S, M, L, XL) printed on body region 20 (for positioning spine portion 30). Tabs 34 can be attached to connect spine portion 30 onto body portion 20 at the preferred (i.e.: S, M, L, XL) location corresponding to the size of the patient's limb. A tension measuring card 80 may also be included in the device as sold. The tension measuring card 80 has scales relating to the size of the patient's limb. Tension measuring card 80 relates the distance that the garment is stretched to the tension in the garment bands by measuring the spacing between lines printed on the garment as the garment is stretched.

Figure 11A:
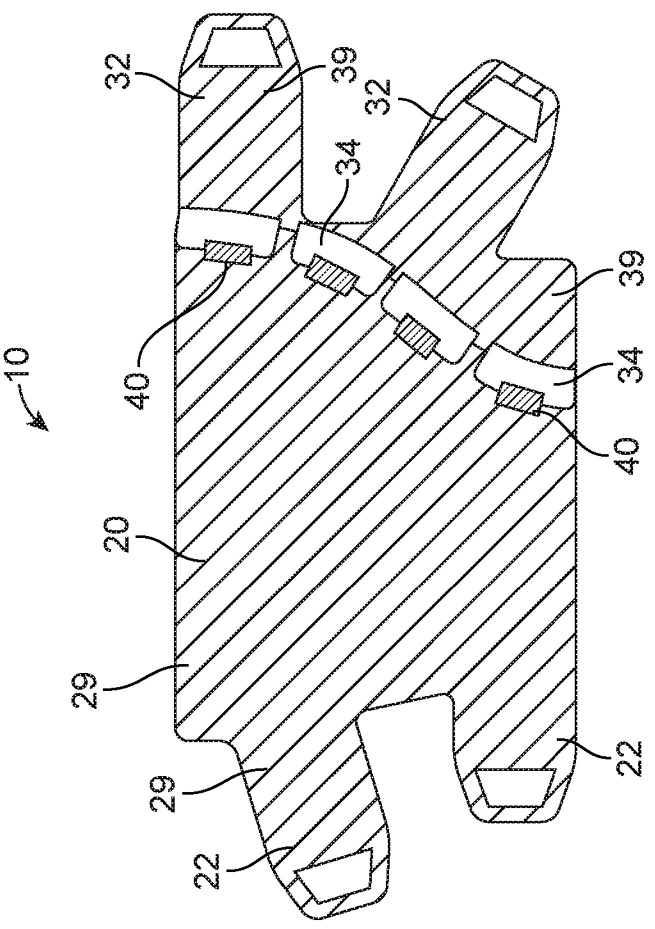
FIG. 11A is a seventh embodiment of the present invention.
Figure 11D:
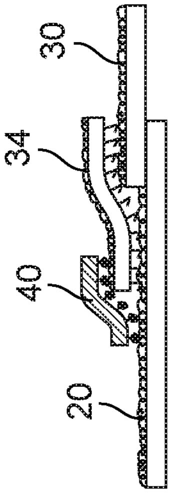
FIG. 11D is a profile view of spine tab hook attachment including stay of the garment of FIG. 11A.
Figure 11C:
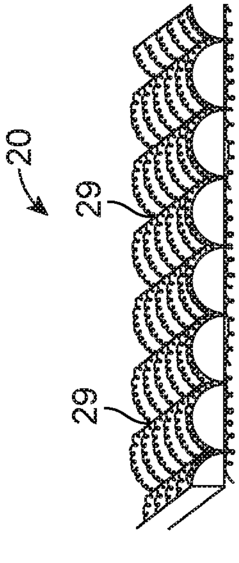
FIG. 11C is a profile view of a portion of the garment of FIG. 11A.
Figure 11B:
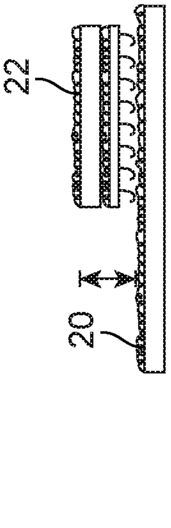
FIG. 11B is a profile view of a band tab hook attachment of the garment of FIG. 11A.

FIG. 11A is a seventh embodiment of the present invention in which garment 10 (i.e.: both body portion 20 and spine portion 30) are made of a thick material such as foam laminate with directional seams 29 and 39 are sewn in to create alternating channels of high and low pressure running along the interior of the garment along the body limb. Such alternating channels of high and low pressure may facilitate drainage of lymphatic fluids. Velcro® stays 40 may be used to further secure tabs 34 to body portion 20. FIG. 11D shows a close-up profile view of this attachment. FIG. 11B is a profile view of the attachment of band 22 back onto body portion 20 (after the end of band 22 has been juxtaposed between two bands 32). FIG. 11C is a profile view of a portion of the garment of FIG. 11A showing directional seams 29 running along body portion 20. As can be seen, the vertical profile (i.e.: thickness) of the connection in FIG. 11B is higher than the vertical profile (i.e.: thickness) of the connection in FIG. 11D. This can be advantageous in that it makes it easier to detach the bands 22 and 32 than to detach the body and spine portions 20 and 30. In this embodiment, the bands 22 and 32 extending across the front of the body limb adhere with a lesser strength than the attachment of the spine and body portions 20 and 30 across the back of the body limb.

Figure 12A:
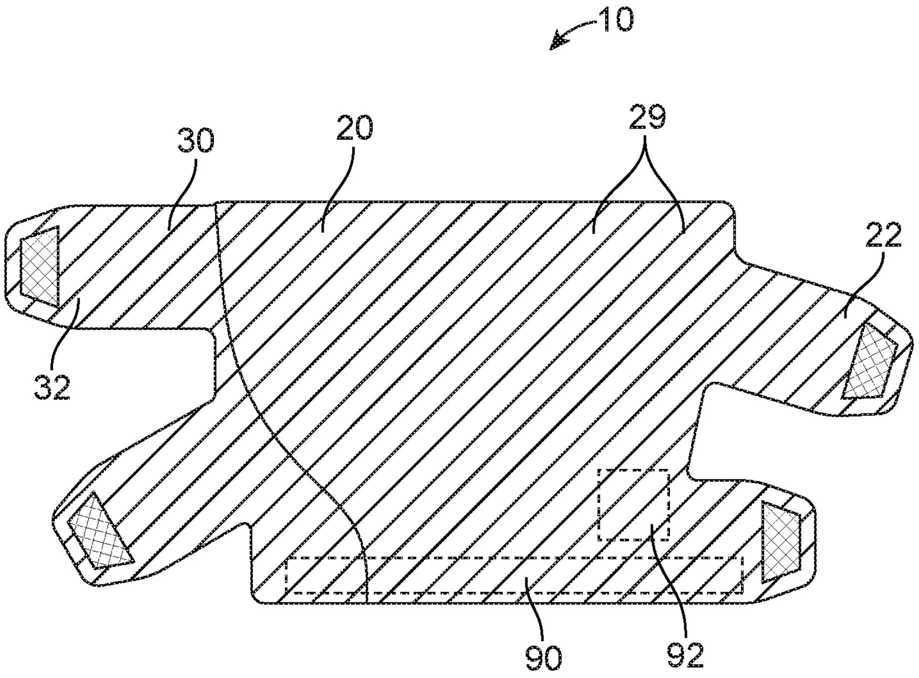
FIG. 12A is a reverse side view of the garment shown in FIG. 11A.
Figure 12B:
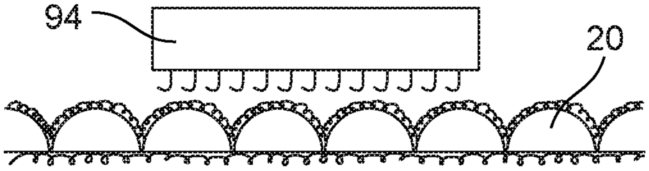
FIG. 12B is a profile view of a portion of the garment of FIG. 12A.

FIG. 12A is a reverse side view of the garment shown in FIG. 11A. The dotted area 90 is an area where an optional bladder or foam may be added to distribute pressure. Similarly, area 92 represents a region where an ulcer is often present (just above the ankle) and spot pressure is required. Foam or bladder piece 94 is positioned in dotted area 90 FIG. 12B is a corresponding profile view.

Figure 13B:
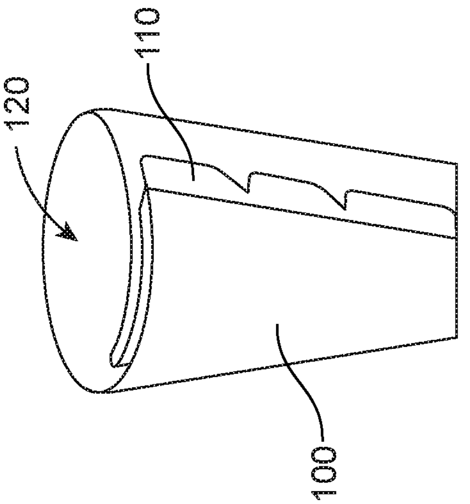
FIG. 13B is the garment of FIG. 13A in a closed position (with the bands removed for clarity of illustration).
Figure 13A:
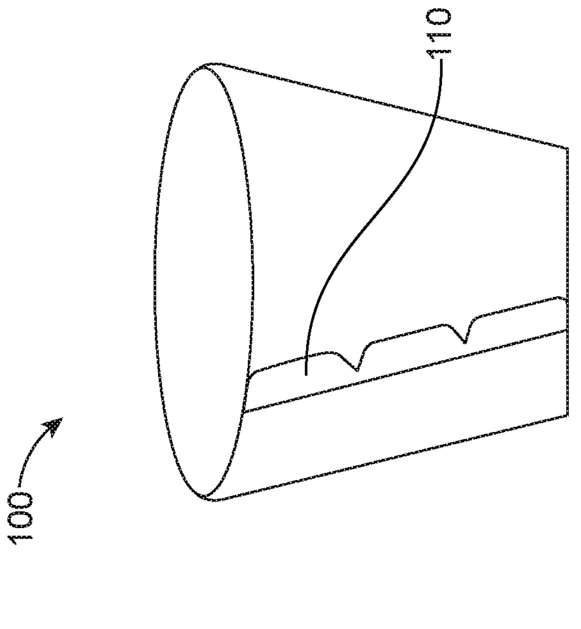
FIG. 13A is an eighth embodiment of the present invention in an open position (with the bands removed for clarity of illustration).
Figure 13C:
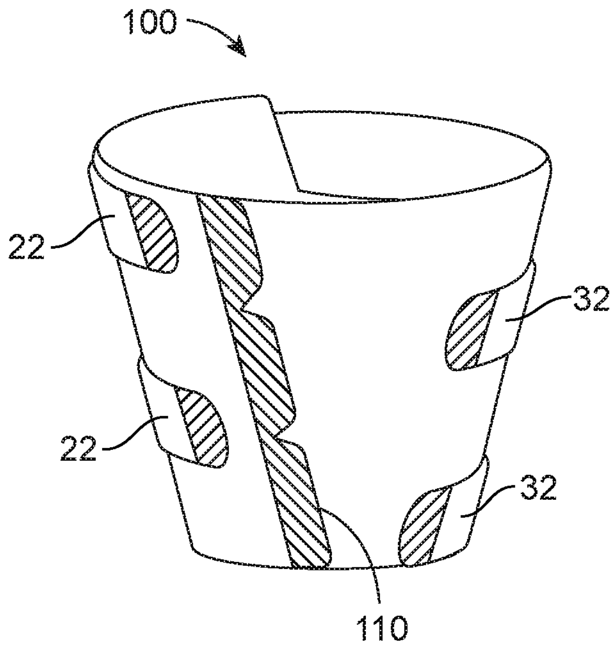
FIG. 13C is an illustration corresponding to FIG. 13A (with the bands shown).
Figure 13D:
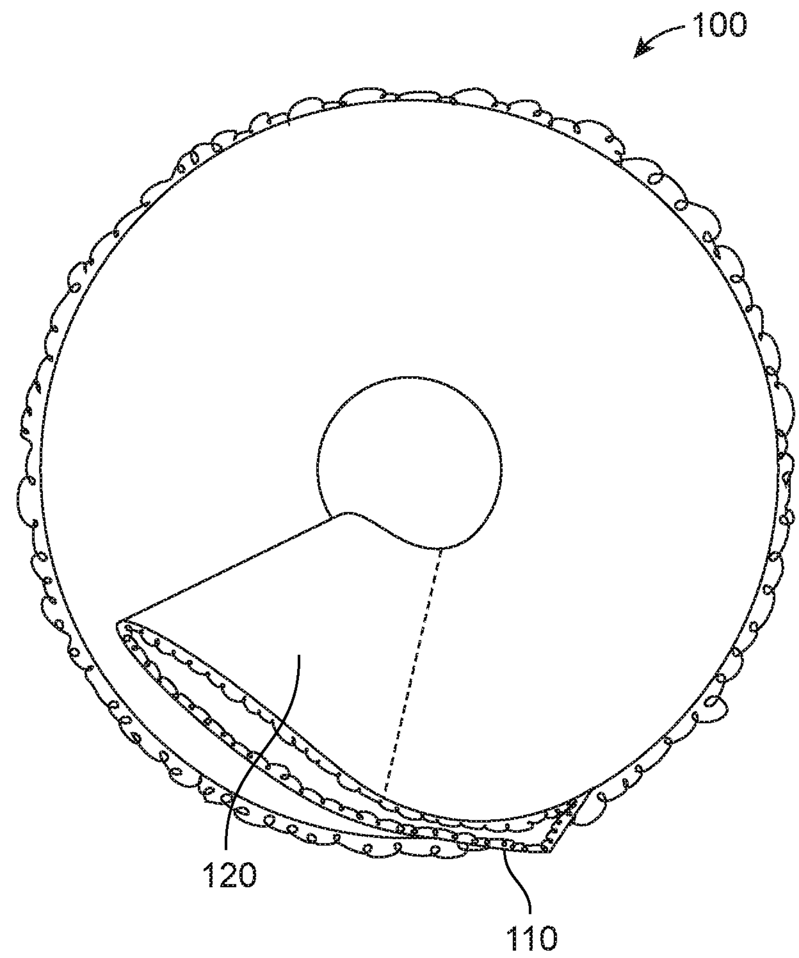
FIG. 13D is a top plan view corresponding to FIG. 13B.

FIG. 13A is simplified view of an eighth embodiment of the present invention in an open position. FIG. 13B is the garment of FIG. 13A in a closed position. In this embodiment, garment 100 is a one-piece cylindrical structure. In FIGS. 13A and 13B, the exterior straps of the garment have been removed for clarity of illustration. The exterior straps are shown in FIG. 13C). The device is first supplied as shown in its "open" position of FIGS. 13A and 13C. An adhesive tab 110 is provided on the outside of the cylindrical device. Garment 100 is either placed on the body limb, and then "closed" to the position shown in FIG. 13B; or alternatively, garment 100 may be closed and then fitted over the body limb. In operation, adhesive tab 110 (which may comprise Velcro®) is simply pulled forward and attached onto the body of the cylinder, as shown. This causes garment 100 to be folded over onto itself (to the position of FIG. 13B), thereby narrowing the circumference of the garment (such that it applies therapeutic pressure to the limb). Similar to the embodiments described above, the positioning of adhesive tab 110 may be set such that it best conforms to the shape of the particular patient's limb. Therefore, measurement indicia may be printed on the outside of garment 100 (either along the top and bottom edges and/or along the mid section of garment 100). The user therefore simply moves adhesive tabs 110 to a preferred position corresponding to the measurement indicia. For some patients, the top tab 110 may be moved farther forward before being attached to garment 100 (e.g.: if the patient has a thinner calf). For some patients, the bottom tab 110 may be moved farther forward before being attached to garment 100 (e.g.: if the patient has a thinner ankle region). FIG. 13C shows exterior bands or straps 22 and 32 (which are attached to the exterior of the garment on the opposite side as shown in FIG. 13C). Bands 22 and 32 are used to tighten the garment around the patient's limb, using the same system as was described above. FIG. 13D corresponds to FIG. 13B and shows the folded over section 120 when garment 100 is moved to its "closed" position about the body limb. It is to be understood that in various embodiments of the device, folded over section 120 may be trimmed off and removed for patient comfort. This would result in a garment operating essentially the same as a two-piece (spine and body) device as described above.

We claim:

1. A therapeutic compression garment for a human, comprising:

a body portion having a first side and an opposing second side with a plurality of bands extending from the first side;

a spine portion having a first side and an opposing second side with a plurality of bands extending from the first side; and a plurality of fastener tabs, wherein the plurality of bands extending from the first side of the body portion and the plurality of bands extending from the first side of the spine portion are flexible and operable configured to wrap around a limb of the human so that the plurality of bands of the body portion are attachable to the spine portion or the body portion, and the plurality of bands of the spine portion are attachable to the body portion or spine portion, and wherein the plurality of bands of the body portion are positioned juxtaposed between the plurality of bands of the spine portion; and wherein the opposing second side of the spine portion is further releasably attached with the opposing second side of the body portion by releasably positioning each of the plurality of fastener tabs at positions at the opposing second side of the body portion and the opposing second side of the spine portion, each of the plurality of fastener tabs being adapted for independent angling and positioning at the opposing second sides of the body portion and the spine portion, and each of the plurality of fastener tabs being configured to connect the opposing second sides of the body portion and the spine portion so that the opposing second sides of the body portion and the spine portion are fastened together and adapted to a contour of the limb of the human.

2. The therapeutic compression garment of claim 1, wherein the body portion is marked with measurement indicia adapted to correspond to a circumference of the limb.

3. The therapeutic compression garment of claim 1, further comprising one or more releasable reinforcement tab, wherein the releasable reinforcement tab is adapted to be releasably secured to at least a portion of one or more of the plurality of fastener tabs.

4. A method of fitting assembling and donning a therapeutic compression garment, comprising:

assembling a therapeutic garment around a body limb of a human, wherein the garment comprises a body portion having a first side and an opposing second side with a plurality of bands extending from the first side, a spine portion having a first side and an opposing second side with a plurality of bands extending from the first side, and a plurality of fastener tabs, the plurality of bands being operable to be wrapped around the body limb, the assembling comprising:

aligning the opposing second side of the spine portion with the opposing second side of the body portion by positioning top and bottom ends of the opposing second sides of the spine portion and the body portion in alignment with each other;

trimming the flexible body portion to match a contour of the body limb independent of any adjustment to the plurality of bands of the spine portion of the plurality of bands of the body portion; and independently angling and positioning each of the plurality of fastener tabs at the opposing second sides of the body portion and the spine portion to fasten together the opposing second sides of the body portion and the spine portion to create an assembled garment that is adjusted to a contour of the limb of the human independent of any adjustment to the plurality of bands; and donning the therapeutic compression garment by wrapping the assembled garment around the body limb, unrolling and adjusting each of the plurality of bands in juxtaposition, and attaching each of the plurality of bands to the assembled garment to secure the garment.

5. The method of claim 4, further comprising discarding the trimmed portion of the body portion after trimming the flexible body portion.

6. The method of claim 4, further comprising attaching one or more releasable reinforcement tab to the assembled garment, wherein the releasable reinforcement tab is releasably secured to at least a portion of one or more of the plurality of fastener tabs.

7. The method of claim 4, further comprising adjusting the plurality of bands of the spine portion and the plurality of bands of the body portion to apply a prescribed amount of compression to the body limb.

8. The method of claim 4, wherein the assembling and the donning steps are capable of being conducted in less than five minutes.

* * * * *